United States Patent [19]
>
> Hanessian

[11] 4,247,687

[45] Jan. 27, 1981

[54] AMINOGLYCOSIDE ANTIBIOTIC DERIVATIVES AND PROCESS FOR THEIR PREPARATION

[75] Inventor: Stephen Hanessian, Beaconsfield, Canada

[73] Assignee: Farmitalia Carlo Erba S.p.A., Milan, Italy

[21] Appl. No.: 47,911

[22] Filed: Jun. 12, 1979

[51] Int. Cl.³ .............................................. C07H 15/22
[52] U.S. Cl. ..................................... 536/12; 424/180; 536/10; 536/17 R
[58] Field of Search ........................... 536/12, 17, 17 R

[56] References Cited

U.S. PATENT DOCUMENTS

| | | |
|---|---|---|
| 4,024,332 | 5/1977 | Fenner et al. ............................ 536/12 |
| 4,065,615 | 12/1977 | Horii et al. .............................. 536/12 |
| 4,125,707 | 11/1978 | Arcamone et al. ..................... 536/12 |

FOREIGN PATENT DOCUMENTS 1488420  10/1977  United Kingdom ...................... 536/12

*Primary Examiner*—Johnnie R. Brown
*Attorney, Agent, or Firm*—Stevens, Davis, Miller & Mosher

[57] ABSTRACT

A process is disclosed for preparing 4'-deoxy-neomycin B, having the formula:

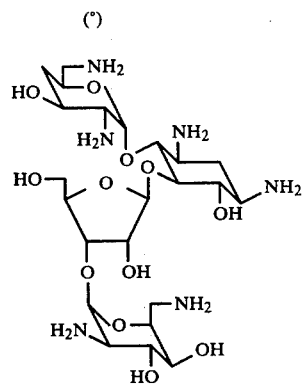

(*)

(*)The conformation of the 2,6-diamino-2,6-dideoxy-β-L-idopyranosyl moiety is arbitrarily chosen among several possible conformations starting from a selectively protected paromomycin derivative having only two free hydroxy groups at C-4' and C-6'.

Chlorination with sulphuryl chloride in pyridine gives the corresponding 4'-6'-dichloro analog which is selectively dechlorinated at position 4' with tributyltin hydride. The 6'-chloro group is then subjected to azidolysis to introduce an azido group. De-O-benzoylation of the resulting 6'-azido derivative, followed by hydrogenolysis, gives 4'-deoxy neomycin B. The new compound displays an antibacterial activity with a higher grade and broader spectrum when compared with those of neomycin B and paromomycin I.

6 Claims, No Drawings

AMINOGLYCOSIDE ANTIBIOTIC DERIVATIVES AND PROCESS FOR THEIR PREPARATION

The present invention relates to new aminoglycoside antibiotics and to a process for their preparation.

More particularly, the invention relates to 4'-deoxyneomycin B (8), a new semisynthetic antibacterial agent.

This invention also relates to certain novel intermediates starting from paromomycin (1) and used in the preparation of the desired 4'-deoxy-neomycin B (8).

The most straightforward approach to improving the spectrum of antibacterial activity of natural aminoglycoside antibiotics has been to remove or sterically hinder sites of enzymatic inactivation.

It is known that the hydroxyl group at the 3'-position in neomycins and related antibiotics is suspectible to enzymatic inactivation by phosphotransferase enzymes produced by resistant bacterial strains, and also that the absence of this hydroxyl group leads to enhanced activity (Kirk-Othmer: *Encyclopedia of Chemical Technology*, Vol. 2, Third Ed. 1978, by John Wiley and Sons Inc.)

Since the adjacent 4'-hydroxyl group might be intimately involved in binding the inactivating enzymes, its removal might be expected to lead to weaker binding and aberrant recognition. This feature has been confirmed by the antibacterial activity of 4'-deoxy-neomycin B (8) which is higher and broader when compared with that of neomycin B.

The starting material of the process described in the present invention is paromomycin (1), a natural aminoglycoside antibiotic, whose properties have been described in U.S. Pat. No. 2,916,485 by Frohart et al and in U.S. Pat. No. 3,065,147 by Arcamone et al. 4'-6'-O-Benzylidene-penta-N-benzoyloxycarbonylparomomycin is prepared, following the procedure described by Hanessian et al in *Tetrahedron Letters*, 4009 (1974) and in *Canadian J. Chem.* 56, 1482 (1978), starting from paromomycin.

O-Benzoylation gives the corresponding hexa-O-benzoylderivative (2), which after hydrolysis of the O-benzylidene group gives the intermediate (3) containing two free hydroxyl groups at C-4' and C-6'.

Chlorination with sulphuryl chloride in pyridine affords the corresponding 4',6'-di-chloro-di-deoxy analog (4) which is selectively dechlorinated at position 4' with tributyltin hydride in toluene in the presence of azobisisobutyronitrile to give the 4'-deoxy derivative (5).

The 6'-chloro group is then subjected to azidolysis in N,N-dimethylformamide to give the 6'-azido compound (6) which, after de-O-benzoylation, affords 6'-azido-4',6'-dideoxy-penta-N-benzoyloxycarbonyl paromomycin (7).

Catalytic hydrogenolysis in acidic dioxane in the presence of 10% palladium-on-charcoal followed by column purification on ionic exchange resins gives the desired 4'-deoxy-neomycin B (8).

Antibacterial Activity

4'-Deoxy-neomycin B (8) displays an antibacterial "in vitro" activity higher and broader when compared with those of neomycin B and paromomycin (1) as reported in Table 1. The antibacterial activity is determined by the conventional agar dilution method, and the minimal inhibitory concentration (MIC) is expressed in mcg/ml.

TABLE 1

Antibacterial activity of 4'-Deoxy-neomycin (8)

| | MIC mcg/ml | | |
|---|---|---|---|
| | 8 | Neomycin B | Paromomycin (1) |
| *Staphylococcus aureus* 209 P | 0.77 | 1.55 | 1.55 |
| *Escherichia coli* K 12 | 3.12 | 6.25 | 12.5 |
| *E. coli* K 12 R 112 (NPT I) | >200 | >200 | >200 |
| *E. coli* K 12 R 118 (NPT II) | 25 | 200 | 200 |
| *E. coli* K 12 R 55 (GNT) | 3.12 | 6.25 | 12.5 |
| *Pseudomonas aeruginosa* 9229 | 25 | 100 | >100 |
| *P. aeruginosa* 19660 | 25 | 50 | >100 |
| *P. aeruginosa* 4 | 12.5 | 25 | >100 |
| *P. aeruginosa* 5 | 25 | 50 | >100 |
| *P. aeruginosa* 6 | 12.5 | 25 | >100 |
| *P. aeruginosa* B | 25 | >100 | >100 |
| *P. aeruginosa* 47823 | 12.5 | >100 | >100 |
| *P. aeruginosa* 53825 | 50 | >100 | >100 |
| *P. aeruginosa* 53585 | 25 | >100 | >100 |
| *Proteus vulgaris* | 12.5 | 25 | 50 |
| *Proteus mirabilis* 525 | 6.2 | 12.5 | 25 |
| *P. mirabilis* V 15 | 12.5 | 25 | 25 |
| *P. sp.* V 16 | >100 | >100 | >100 |

EXAMPLE 1

Penta-N-Benzyloxycarbonyl paromomycin, 6,3',2",5",3'",4'"-hexabenzoate (3) prepared according to S. Hanessian et al, *Canadian J. Chem.* 56, 1482 (1978) starting from paromomycin (yield 92%)

A solution containing 25.8 g of penta-N-benzyloxycarbonylparomomycin in 217 ml of dry benzaldehyde was cooled to 0° C. and treated with 77 ml of 98% formic acid dropwise. After standing overnight at 5° C., the solution was added slowly and with efficient stirring to an aqueous solution of sodium bicarbonate. The mixture was extracted with chloroform, the extracts were processed as usual and the evaporated residue was triturated with petroleum ether to precipitate the title compound. Yield 27.3 g of an amorphous white solid which is chromatographically homogeneous except for traces of minor impurities. The physical constants of a purified sample agreed with those in the literature (*Can. J. Chem.* 56, 1482 (1978); *Tetrahedron Letters* 4009, 1974).

Benzoylation of this compound (27.3 g) was effected in pyridine (230 ml) with benzoyl chloride (15.5 ml). After stirring at room temperature for 2 hours, the mixture was stirred at 60° C. for 72 hours. The mixture was then poured into ice-water, extracted with chloroform and the extracts were evaporated to dryness.

The residual material containing 2 is used as such for the subsequent step. The residue is dissolved in 150 ml of glacial acetic acid and 10 ml of water was added. The solution was heated at 90° C. for 6 hours, then it was evaporated to dryness by azeotropic distillation in the presence of toluene. The final residue was triturated with 2-propyl ether and the solid was filtered. Chromatography on silica gel (chloroform-ethyl acetate, 20:5) removes some non-polar minor impurities.

Development with chloroform-ethyl acetate-methanol (20:5:0.5) gave the title compound (3), as a foam. Yield 14.5 g (40% overall from paromomycin).

EXAMPLE 2

Chlorination of (3)

The preceding compound (4 g) was dissolved in 40 ml of dry pyridine and the cooled solution was treated with 4 ml of sulfuryl chloride dropwise and under a nitrogen atmosphere. After stirring 1 hour at 0° C. and 48 hours at room temperature, the solution was treated with aqueous sodium bicarbonate. Processing was done in the usual manner by extraction with chloroform, washing the extracts with water, drying and evaporation to dryness. The residue was chromatographed on silica gel (chloroform-ethyl acetate, 20:5) to give 2.5 g of a pale yellow solid (compound 4).

Anal. Calc.: C 64.48; H 4.87; N 3.60; Cl 3.64. Found: C 64.48; H 5.11; N 3.70; Cl 3.67.

EXAMPLE 3

Selective Reduction of 4

The preceding product (1.25 g) was dissolved in 26 ml of toluene and the solution was treated with 0.65 ml of tributyltin hydride and 30 mg of azobisisobutyronitrile. After stirring for 2 hours at 80°–85° C. (monitored by t.l.c.) the solution was evaporated to dryness and the residue was chromatographed on silica gel (chloroform-ethyl acetate, 21:4) to give 850 mg of a white amorphous solid (69%) corresponding to the 4'-deoxy derivative (5). If the reduction is continued some dideoxy product is also formed.

Anal. Calc.: C 66.01; H 5.01; N 3.66. Found: C 65.64; H 5.31; N 3.80.

EXAMPLE 4

6'-Azido-4',6'-dideoxy-penta-N-benzyloxycarbonyl paromomycin perbenzoate (6)

The preceding compound (600 mg) in 10 ml of dry dimethylformamide containing 40 mg of sodium azide was heated at 90° C. with stirring for two days under nitrogen. The mixture was evaporated to dryness, the residue was suspended in chloroform, the solution washed with water and the organic phase was processed as usual to give a solid which was chromatographed on silica gel (chloroform-ethyl acetate, 20:5). The title compound was obtained as a white amorphous solid (490 mg, 81%). This compound has a slightly lower Rf than the chloro precursor (5).

EXAMPLE 5

6'-Azido-4',6'-dideoxy-penta-N-benzyloxycarbonyl paromomycin (7)

The preceding compound (350 mg) was dissolved in methanol and the solution was treated with a solution of sodium methoxide (freshly prepared), until a pH of ≃8 was reached. The solution was stirred at room temperature for 3 days (with t.l.c. monitoring), then neutralized with Dowex-50 (H+), filtered and evaporated to dryness. The residue was chromatographed on silica gel (chloroform-ethyl acetate-methanol, 20:5:2), to give the title compound as a white amorphous powder, yield 170 mg (72%).

Anal. Cal.: $C_{63}H_{74}N_8O_{22}$; C 58.42; H 5.76; N 8.65. Found: C 58.32; H 5.86; N 7.99.

Care should be taken with the debenzoylation process to avoid strongly basic pH's.

EXAMPLE 6

4'-Deoxyneomycin (8)

A solution containing the preceding compound (114 mg) in 200 ml of dioxane containing 0.5 ml N HCl was hydrogenated in the presence of 10% Pd-C (120 mg) for 10 hours. The catalyst was filtered and the filtrate was evaporated to dryness. The residue was dissolved in water and passed through a Dowex 1×8 (OH−) column, the effluent was evaporated, and the residue was separated on CG-50 ($NH_4^+$, 100–200 mesh) to give the title compound as an amorphous powder (39 mg). The product was homogeneous in the solvent system chloroform-methanol-conc-$NH_4OH$ (1:3:2) and had an Rf of 0.4 (neomycin Rf∼0.3); [α]+36° (c 0.9, $H_2O$).

The complete reaction scheme illustrating the foregoing is as follows:

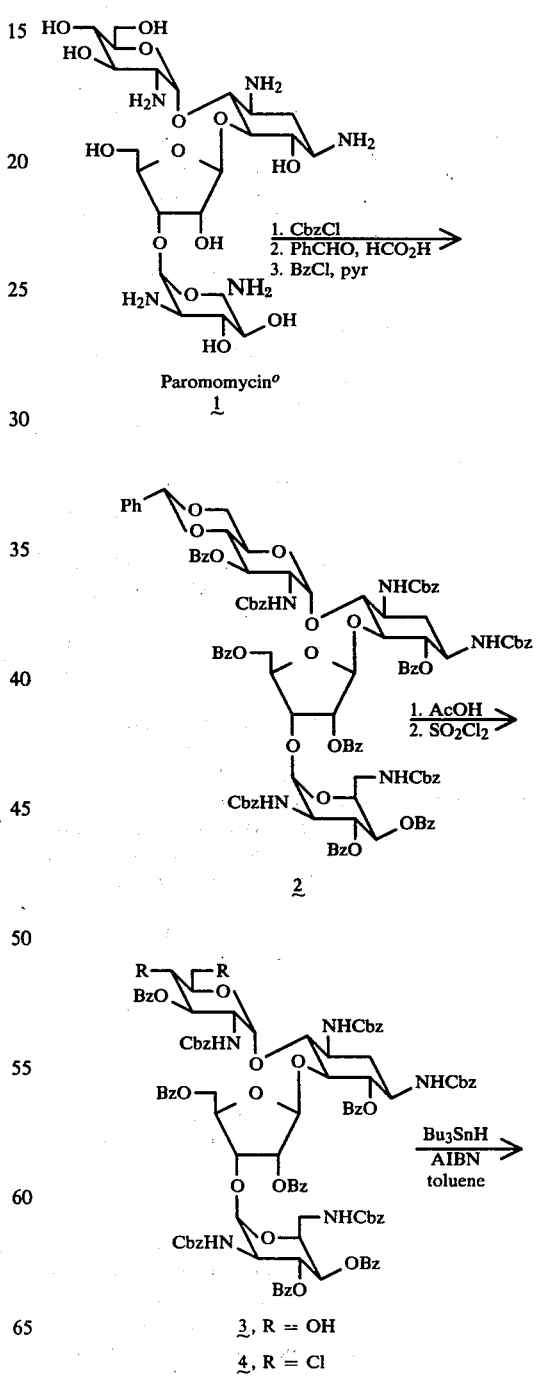

-continued

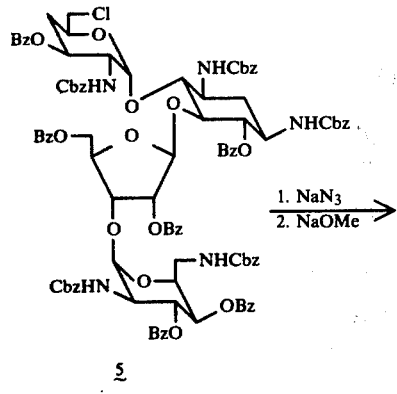

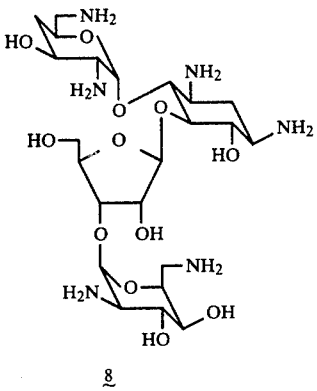

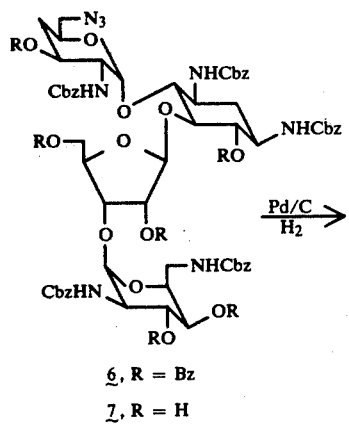

*a*The conformation of the 2,6-diamino-2,6-dideoxy-β-L-idopyranosyl moiety is arbitrarily chosen among several possible conformations.

What is claimed is:
1. A compound selected from the class consisting of: 4′,6′-dichloro-4′,6′-dideoxy-penta-N-benzyloxycarbonyl-4′-epi-paromomycin-perbenzoate; 6′-chloro-4′,6′-dideoxy-penta-N-benzyloxycarbonyl-paromomycin-perbenzoate; 6′-azido-4′,6′-dideoxy-penta-N-benzyloxycarbonyl-paromomycin-perbenzoate; and 6′-azido-4′,6′-dideoxy-penta-N-benzyloxycarbonyl-paromomycin.

2. 4′,6′-dichloro-4′,6′-dideoxy-penta-N-benzyloxycarbonyl-4′-epi-paromomycin-perbenzoate.

3. 6′-chloro-4′,6′-dideoxy-penta-N-benzyloxycarbonylparomomycin-perbenzoate.

4. 6′-azido-4′,6′-dideoxy-penta-N-benzyloxycarbonyl-paromomycin-perbenzoate.

5. 6′-azido-4′,6′-dideoxy-penta-N-benzyloxycarbonyl-paromomycin.

6. A process for preparing 4′-deoxyneomycin B, comprising the following steps:
(a) subjecting paromomycin (1) to O-benzylation with benzoyl chloride to give the corresponding hexa-O-benzoyl derivative (2);
(b) subjecting (2) to hydrolysis by heating in the presence of glacial acetic acid to give the intermediate (3) having two free hydroxyl groups at C-4′ and C-6′;
(c) chlorinating (3) with sulfuryl chloride to give the corresponding 4′,6′-dichloro-di-deoxy analog (4);
(d) selectively dechlorinating (4) at C-4′ with tributyl tin hydride in the presence of azobisisobutyronitrile to give the 4′-deoxy derivative (5);
(e) subjecting (5) to azidolysis with sodium azide to convert the 6′-chloro group to the 6′-azido compound (6);
(f) subjecting (6) to de-O-benzoylation with sodium methoxide to give compound (7);
(g) subjecting (7) to catalytic hydrogenolysis in the presence of palladium to give 4′-deoxy-neomycin B (8); and
(h) recovering and purifying the product of the catalytic hydrogenolysis as substantially pure 4′-deoxyneomycin B.

* * * * *

UNITED STATES PATENT AND TRADEMARK OFFICE
CERTIFICATE OF CORRECTION

PATENT NO. : 4,247,687                      Page 1 of 2
DATED      : January 27, 1981
INVENTOR(S) : Stephen HANESSIAN It is certified that error appears in the above-identified patent and that said Letters Patent are hereby corrected as shown below:

IN THE ABSTRACT -

The first line after the asterisked footnote below the structural formula should read as -- Chlorination of penta-N-benzyloxy-carbonyl-6,3',2",5",3'",4'"-hexa-O-benzoyl-paromomycin with sulphuryl chloride in pyridine gives --

Column 1, line 37 should read as follows

Benzylidene-penta-N-benzyloxycarbonylparomomy-

Column 1, line 54 should read as follows

4',6'-dideoxy-penta-N-benzyloxycarbonyl paromomy-

UNITED STATES PATENT AND TRADEMARK OFFICE
CERTIFICATE OF CORRECTION

PATENT NO. : 4,247,687

DATED : January 27, 1981

INVENTOR(S) : Stephen HANESSIAN

It is certified that error appears in the above-identified patent and that said Letters Patent are hereby corrected as shown below:

Column 4, first structural formula, in the bottom ring the right hand amino radical ($NH_2$) should be shown as connected to the ring as follows:

instead of: 

Signed and Sealed this

*First* Day of *September 1981*

[SEAL]

*Attest:*

GERALD J. MOSSINGHOFF

*Attesting Officer*     *Commissioner of Patents and Trademarks*